US012582623B2

(12) United States Patent
van Dijk-Ottens et al.

(10) Patent No.: US 12,582,623 B2
(45) Date of Patent: Mar. 24, 2026

(54) COMPOSITION COMPRISING EPA, MA AND LEUCINE FOR IMPROVING MUSCLE FUNCTION

(71) Applicant: N.V. Nutricia, Zoetermeer (NL)

(72) Inventors: Miriam van Dijk-Ottens, Utrecht (NL); Francina Jeannette Dijk, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 796 days.

(21) Appl. No.: 17/770,634

(22) PCT Filed: Oct. 30, 2020

(86) PCT No.: PCT/NL2020/050676
§ 371 (c)(1),
(2) Date: Apr. 21, 2022

(87) PCT Pub. No.: WO2021/086190
PCT Pub. Date: May 6, 2021

(65) Prior Publication Data
US 2022/0288002 A1      Sep. 15, 2022

(30) Foreign Application Priority Data

Oct. 31, 2019    (WO) ................ PCT/NL2019/050717

(51) Int. Cl.
| | |
|---|---|
| *A61K 31/198* | (2006.01) |
| *A23L 33/12* | (2016.01) |
| *A23L 33/155* | (2016.01) |
| *A23L 33/175* | (2016.01) |
| *A23L 33/19* | (2016.01) |
| *A61K 31/20* | (2006.01) |
| *A61K 31/202* | (2006.01) |
| *A61K 47/42* | (2017.01) |
| *A61P 21/06* | (2006.01) |

(52) U.S. Cl.
CPC ........... *A61K 31/198* (2013.01); *A23L 33/12* (2016.08); *A23L 33/155* (2016.08); *A23L 33/175* (2016.08); *A23L 33/19* (2016.08); *A61K 31/20* (2013.01); *A61K 31/202* (2013.01); *A61K 47/42* (2013.01); *A61P 21/06* (2018.01)

(58) Field of Classification Search
CPC .... A61K 31/198; A61K 31/20; A61K 31/202; A23L 33/12; A23L 33/175; A23L 33/19; A61P 3/02
See application file for complete search history.

(56) References Cited

U.S. PATENT DOCUMENTS

| | | | |
|---|---|---|---|
| 2002/0099020 A1* | 7/2002 | Abbruzzese | A61K 9/0029 514/474 |
| 2011/0152184 A1* | 6/2011 | van Norren | A61K 31/202 514/5.6 |

FOREIGN PATENT DOCUMENTS

| | | |
|---|---|---|
| WO | 2006/085144 A2 | 8/2006 |
| WO | 2012/141575 A1 | 10/2012 |

OTHER PUBLICATIONS

ClevelandClinic https://my.clevelandclinic.org/ health/diseases/ 23167-sarcopenia, see p. 12, 2022 (Year: 2022).*
Nationwide Children's Hospital (https://www.nationwidechildrens. org/conditions/muscular-dystrophy, 2025) (Year: 2025).*
Novartis Medical Nutrition: "Resource (R) Support: specialized nutrition for people with cancer", Novartis Medical Nutrition, Jan. 1, 2003 (Jan. 1, 2023), pp. 1-36, XP055346865 Retrieved from the Internet: URL:https://WWW.nestle.com/investors/overview/mergers-and-acquisitions/boost [retrieved on Feb. 16, 2017].
Soni et al: "Eicosapentaenoic and Docosahexaenoic Acid-Enriched High Fat Diet Delays Skeletal Muscle Degradation in Mice", Nutrients, vol. 8, No. 9, Sep. 3, 2016 (Sep. 3, 2016), p. 543 XP055705761, DOI: 10.3390/nu8090543.
Liu et al: "Fish Oil Enhances Intestinal Integrity and Inhibits TLR4 and N0D2 Signaling Pathways in Weaned Pigs after LPS Challenge", The Journal of Nutrition, vol. 142, No. 11, Sep. 26, 2012 (Sep. 26, 2012), pp. 2017-2024, XP055705758, US, ISSN: 0022-3166, DOI: 10.3945/jn.112.164947.

* cited by examiner

*Primary Examiner* — Umamaheswari Ramachandran
(74) *Attorney, Agent, or Firm* — Ipsilon USA—NLO

(57) ABSTRACT

The invention relates to compositions comprising EPA, MA and leucine for prevention and/or treatment of a disease or condition involving muscle decline or for improving muscle function.

15 Claims, 1 Drawing Sheet

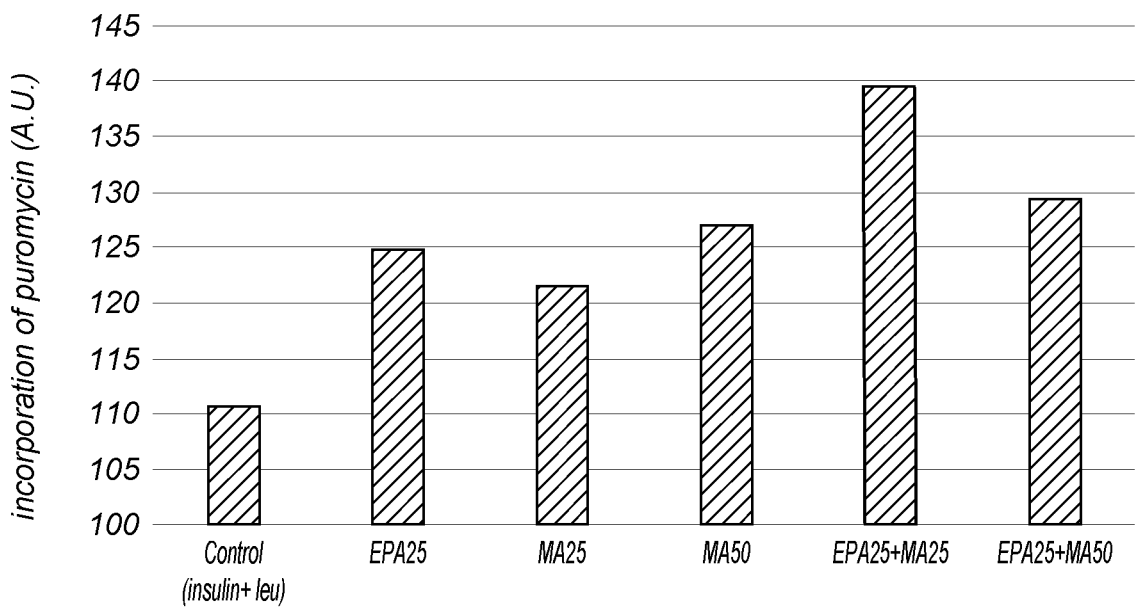

COMPOSITION COMPRISING EPA, MA AND LEUCINE FOR IMPROVING MUSCLE FUNCTION

FIELD OF THE INVENTION

The present invention relates to compositions for prevention and/or treatment of a disease or condition involving muscle decline or for improving muscle function.

BACKGROUND OF THE INVENTION

There are many causes of muscle loss. Sarcopenia, for instance, is the syndrome of loss of muscle due to aging. From the age of about 30, humans lose 3-8% of muscle per decade and this accelerates after 60 years of age. Muscle loss can also be the result of inactivity due to bed rest, physical trauma treatment (such as fractures) or impaired mobility. Alternatively, muscle loss can be due to insufficient muscle protein synthesis or to muscle degradation.

There is a lot of information available on the prevention of sarcopenia, the stimulation of muscle growth and the stimulation of muscle protein synthesis. It is, for instance, known that leucine and/or vitamin D have a positive impact on muscle growth. It is furthermore also known that specific fatty acids can have a benefit on muscle protein mass or delaying muscle degradation.

Lui et al. (J. Nutr. 142: 2017-2024, 2012) disclose that fish oil increases muscle protein mass. The fish oil diet used by Lui et al. comprises 5.3% of MA, 11.6% of EPA and 7.9% DHA, with an implicit ratio of EPA over MA of 2.2.

Soni et al. (Nutrients 2016, 8, 543) disclose that EPA and DHA can delay skeletal muscle degradation. In this study the high fat diet with EPA and DHA comprises 4.58 mg MA per g diet, 2.03 mg EPA per g diet and 4.58 mg DHA per gram diet. Hence the implicit ratio of EPA over MA is 0.44. No weight is given to the relative amounts of EPA and MA.

Hitherto, as muscle loss continues to be a challenge, there is a need for further improved compositions to prevent, or treat muscle loss and to rebuild the lost muscle.

SUMMARY OF THE INVENTION

The inventors have surprisingly found that a composition comprising eicosapentaenoic acid (20:5(n-3); EPA), myristic acid (C14:0; MA) and leucine, wherein the EPA and MA are present in a weight ratio in the range of 0.8-1.8 (i.e. 0.8:1-1.8:1), has effects on preventing/treating muscle decline or improving muscle function (particularly in a subject suffering from or at risk of impaired muscle function), which are particularly improved compared to compositions with EPA:MA ratios outside this range. The inventors have shown in an in vitro model that myotubes showed increased muscle protein synthesis when presented with the composition of the invention having the specific range of EPA and MA, compared with myotubes presented with the individual compositions and with a composition having EPA and MA ratios outside this range.

It has particularly been found that EPA and MA ratios in this specific range of the invention yield a benefit on muscle protein synthesis compared to the prior art compositions outside this range. Thus compositions having leucine and EPA and MA in a weight ratio in the range of 0.8-1.8 (i.e. 0.8:1-1.8:1), preferably the range of 0.9-1.7, more preferably in the range of 1.0-1.6 and even more preferably 1.1-1.5, have a benefit on gaining or increasing muscle mass and/or maintaining muscle mass. Preferably the EPA and/or the MA and/or the leucine are at least partly in free form. It is hereby understood that EPA means eicosapentaenoic acid. This is an omega-3 fatty acid that is also denoted as 20:5(n-3). It is also understood that MA means myristic acid, which is a saturated fatty acid having 14 carbon atoms which is also denoted as C14:0.

The composition may be a nutritional composition and/or a ready-to-eat composition. Alternatively the composition can be a dietary supplement.

In a preferred embodiment the composition comprises further ingredients such as proteins, further anabolic amino acids, fibres and micronutrients.

The composition may be administered to healthy persons in order to prevent muscle decline. This could be relevant if a person is inactive and muscle loss is expected. Examples of such situations include bed rest and immobilization due to fracture treatment. Alternatively the composition may be administered to a person suffering from muscle decline or from loss of muscle function.

DETAILED DESCRIPTION

The invention encompasses a composition comprising eicosapentaenoic acid (C20:5(n-3); EPA), myristic acid (C14:0; MA) and leucine (leu) for use in prevention and/or treatment of a disease or condition involving muscle decline, wherein the composition comprises EPA and MA in a weight ratio in the range of 0.8-1.8 (i.e. 0.8:1-1.8:1). The invention also encompasses a composition comprising EPA, MA and leucine for use in improving muscle function, wherein the composition comprises EPA and MA in a weight ratio in the range of 0.8-1.8.

Depending on the jurisdiction, the invention could be worded as the use of EPA, MA and leucine for the manufacture of a composition for the treatment of a disease or condition involving muscle decline, wherein the composition comprises EPA and MA in a weight ratio in the range of 0.8-1.8. The invention also encompasses the use of EPA, MA and leucine for the manufacture of a composition for improving muscle function, wherein the composition comprises EPA and MA in a weight ratio in the range of 0.8-1.8. Similarly, the invention may need to be worded as a method for preventing and/or treating a disease or condition involving muscle decline, wherein the method comprises administering a composition comprising EPA, MA and leucine and wherein the EPA and MA are provided in a weight ratio in the range of 0.8-1.8. The invention can also be worded as a (non-therapeutic) method for improving muscle function in a (healthy) subject, wherein the method comprises administering a composition comprising EPA, MA and leucine and wherein the EPA and MA are provided in a weight ratio in the range of 0.8-1.8. Preferably the composition is administered to a person in need thereof, such as described here below.

It is understood that EPA and MA in a weight range of x-y implies that the weight ratio of EPA compared to MA is in said range. Hence said range equals having EPA:MA in a range of x:1-y:1. For instance EPA and MA in the range of 0.8-1.8 is understood as 0.8:1-1.8:1. This principle applies throughout this document.

It is furthermore understood that improving muscle protein is particularly useful in a subject suffering from or at risk of impaired muscle function. The (prophylactic) treatment is targeted at muscle decline in a human, preferably a human of the age of at least 30 years of age, more preferably of the age of at least 50, more preferably of the age of at least 60, and even more preferably of the age of at least 70 years of age. Muscle decline comprises any disease or condition selected from the group of sarcopenia, loss of muscle mass related to aging, muscle atrophy, muscle wasting, insufficient muscle protein synthesis, or any of the conditions listed below in the medical use section. For the present invention prevention implies to prevent the onset of a muscle disease or condition. This should not be interpreted such that the human will not suffer any muscle disease or condition for the remainder of its life, but rather the prevention of a muscle disease or condition when the human is at risk of or at increased risk of said muscle disease or condition. Hence preferably the prevention of a muscle disease or condition should be interpreted as the prevention of a muscle disease or condition when a muscle disease or condition is expected, which is during or following bed rest, during or following physical trauma treatment (such as fractures), during or following weightlessness, during or following dieting or during or following impaired mobility.

The compositing for use is for improving muscle function in a subject in need thereof. Preferably the subject in need thereof is a human preferably of the age of at least 30 years of age, more preferably of the age of at least 50, more preferably of the age of at least 60, and even more preferably of the age of at least 70 years of age. The subject preferably suffers from sarcopenia, loss of muscle mass related to aging, impaired muscle recovery, muscle damage, muscle proteolysis, muscle atrophy, muscle dystrophy or frailty. Preferably, improving muscle function involves gaining or increasing muscle mass and/or maintaining muscle mass.

Preferably, the composition of the invention is for use in improving muscle protein synthesis.

The composition for use according to the invention can be a nutritional composition implying that it comprises at least 10 en. % of fats, at least 15 en. % of carbohydrates and at least 30 en. % of proteins. The nutritional composition for use can be a sole source of nutrition—meaning that the patient does solely receive the composition of the invention and does not receive any other nutrition—or it can be a nutritional supplement—meaning that it is administered in addition to a regular diet. Preferably the nutritional composition or nutritional supplement comprises less than 30 en. % of fats, less than 35 en. % of carbohydrates and less than 60 en. % of protein. The term en. % is known in the art and refers to the relative energy or caloric content compared to the total calories from fats, carbohydrates and proteins (i.e. en. % of protein+en. % of carbohydrates+en. % of fats=100%). Caloric contents can be calculated based on Atwater constants, using the factors 4 kcal/g for protein, 4 kcal/g for carbohydrates and 9 kcal/g for lipids. Preferably the composition for use also contains micronutrients such as minerals and vitamins.

In another embodiment the composition for use according to the invention is a dietary supplement implying that said composition comprises at least 10 wt. %, more preferably at least 25 wt. %, and even more preferably at least 50 wt. % of the sum of EPA and MA, based on dry weight of the composition. Preferably said composition further comprises at least 10 wt. % more preferably at least 25 wt. %, and even more preferably at least 50 wt. % of leucine, based on dry weight of the composition. Hereby it is understood that a supplement is a composition that is administered along with regular nutrition. A dietary supplement typically comprises only a few active ingredients and is usually formulated for a specific benefit. Compared to nutritional compositions or nutritional supplements, the dietary supplement hence comprises fewer ingredients and the few ingredients in het supplement are therefore provided at high relative levels.

The composition for use according to the invention comprises EPA, MA and leucine, wherein the ratio of EPA:MA: leucine is 0.8-1.2:0.8-1.2:1, provided that the EPA:MA ratio fits the above-described restrictions. Preferably the weight ratio of the sum of EPA and MA compared to the amount of leucine is in the range of 1-2 (i.e. 1:1-2:1), more preferably in the range of 1-1.5. The above numbers are calculated on total leucine in the composition.

Fatty Acids

The composition for use of the invention comprises EPA and MA in a weight ratio in the range of 0.8-1.8 (i.e. 0.8:1-1.8:1). Preferably the weight ratio of EPA and MA is 0.9-1.7, more preferably 1.0-1.6, even more preferably 1.1-1.5. Alternatively it is preferred that the weight ratio of EPA and MA is 1.0-1.8, more preferably 1.1-1.6. It is hereby understood that EPA means eicosapentaenoic acid. This is an omega-3 fatty acid that is also denoted as 20:5(n-3). It is also understood that MA means myristic acid, which is a saturated fatty acid having 14 carbon atoms which is also denoted as C14:0.

According to a preferred embodiment, the composition is a nutritional composition and comprises additional fatty acids besides EPA and MA. Preferably the amount of fatty acid may vary between 10 and 40 en. %, preferably between 20 and 35 en. %. In a preferred embodiment the fatty acid composition comprises 5-50 wt. % of EPA and MA (i.e. the sum of EPA and MA based on total fatty acids). More preferably the fatty acid composition comprises 6-45 wt. % of EPA and MA, even more preferably 8-35 wt. % of EPA and MA, even more preferably 10-25 wt. % of EPA and MA, and even more preferably 11-20 wt. % of the sum of EPA and MA based on total fatty acids in the composition.

Preferably the nutritional composition comprises 1-10 g of EPA per 100 g based on dry weight of the composition and 1-10 g of MA per 100 g based on dry weight of the composition, more preferably 1-5 g of EPA per 100 g based on dry weight of the composition and 1-5 g of MA per 100 g based on dry weight of the composition, provided that the amount of EPA and MA complies with the EPA:MA ratio. Preferably the nutritional composition comprises 0.1-1 g of EPA per 100 ml of the composition and 0.1-1 g of MA per 100 ml of the composition, more preferably 0.3-6 g of EPA per 100 ml of the composition and 0.3-6 g of MA per 100 ml of the composition, provided that the amount of EPA and MA complies with the EPA:MA ratio.

In a preferred embodiment the nutritional composition comprises less than 5 wt. % DHA based on fatty acids. In a more preferred embodiment the composition comprises less than 1 wt. % DHA and in an even more preferred embodiment the composition comprises substantially no DHA. It is hereby understood that substantially implies that DHA is below the detection limit of state-of-the art analysing equipment which is about 0.1 wt. %. It is understood that DHA refers to docosahexaenoic acid, which is an omega-3 fatty acid having a carbon chain of 22 carbon atoms also denoted as C22:6(n-3).

According to another preferred embodiment, the composition is a dietary supplement. In this case the amount of fatty acids can vary between 30-75 en. %, more preferably 40-60 en. %, even more preferably 45-55 en. %. In this case the dietary supplement comprises 50-100 wt. % of EPA and MA, preferably 60-95 wt. % of EPA and MA, even more preferably 70-90 wt. % of EPA and MA, even more preferably 80-85 wt. % of EPA and MA based on fatty acids.

In a further preferred embodiment the dietary supplement comprises less than 5 wt. % DHA based on fatty acids. In a further preferred embodiment the dietary supplement comprises less than 1 wt. % DHA and in an even more preferred embodiment the dietary supplement comprises substantially no DHA. It is hereby understood that substantially implies that DHA is below the detection limit of state-of-the art analysing equipment which is about 0.1 wt. %. In an even further preferred embodiment the dietary supplement comprising EPA and MA does not comprise further omega-3 fatty acids. In a most preferred embodiment the dietary supplement comprising EPA and MA does not comprise further fatty acids.

The fatty acids may be obtained from animal fat, vegetable fat or from a combination of both. Although animal fats such as lard or butter have essentially equal caloric and nutritional values and can be used interchangeably, vegetable oils are highly preferred in the practice of the present invention due to their readily availability and ease of formulation. In one embodiment, the present composition comprises rapeseed oil, corn oil and/or sunflower oil.

Preferably the composition of the invention, the nutritional composition of the invention, the nutritional supplement of the invention or the dietary supplement of the invention are formulated such that the daily dose of EPA is 1-4 grams, preferably 1.5-3 grams and more preferably 1.8-2.4 grams.

In a preferred embodiment the composition of the invention, the nutritional composition of the invention, the nutritional supplement of the invention or the dietary supplement of the invention comprises EPA and/or the MA that is at least partly provided as free fatty acid. In a preferred embodiment at least 50 wt. %, preferably at least 60 wt. %, more preferably at least 70 wt. %, even more preferably at least 80 wt. %, even more preferably at least 90 wt. % and most preferably 100 wt. % (all) of the EPA is provided as free fatty acid. In a preferred embodiment at least 50 wt. %, preferably at least 60 wt. %, more preferably at least 70 wt. %, even more preferably at least 80 wt. %, even more preferably at least 90 wt. % and most preferably 100 wt. % (all) of the MA is provided as free fatty acid. In another preferred embodiment at least 50 wt. %, preferably at least 60 wt. %, more preferably at least 70 wt. %, even more preferably at least 80 wt. %, even more preferably at least 90 wt. % and most preferably 100 wt. % (all) of the EPA and MA is provided as free fatty acid.

Proteinaceous Matter

The composition for use according to the invention comprises proteinaceous matter or protein. In the context of the present invention it is understood that the term 'protein' is synonymous to proteinaceous matter and encompasses intact protein, hydrolyzed protein, free amino acids, anabolic amino acid derivatives and all other forms of proteinaceous matter. Preferably the composition comprises at least 25 en. %, preferably at least 35 en. %, more preferably at least 45 en. %, even more preferably at least 55 en. % of protein. Preferably the composition comprises less than 70 en. %, preferably less than 60 en. % of protein. In a most preferred embodiment, the composition comprises 25-65 en % of protein, more preferably 30-50 en % of protein.

A preferred source of protein is whey protein. Thus the composition for use according to the invention preferably comprises whey protein. In a preferred embodiment the composition comprises at least 50 wt. %, more preferably at least 60 wt. %, even more preferably at least 70 wt. %, even more preferably at least 80 wt. %, even more preferably at least 90 wt. % and most preferably 100 wt. % whey protein based on total protein in the composition.

Whey protein is considered a "fast" protein referring to the rate of appearance in the circulation of the amino acids following whey ingestion. The whey protein may be an intact whey protein, a hydrolysed whey protein, a microparticulate whey protein, a nanoparticular whey protein, a micellar whey protein, and the like. Preferably, the whey protein is an intact whey protein, i.e. a whey protein in its intact form, such as present in fresh milk.

Any commercially available source of whey protein may be used for the current invention. This includes whey obtained by any process for the preparation of whey known in the art, as well as whey protein fractions prepared thereof, or the proteins that constitute the bulk of the whey proteins being β-lactoglobulin, α-lactalbumin and serum albumin, such as liquid whey, or whey in powder form, such as whey protein isolate (WPI) or whey protein concentrate (WPC). The amino acid composition of whey protein depends slightly the type and source of the whey, but whey typically comprises between 10 and 12% of leucine, wherein the leucine is part of the whey protein. Whey protein concentrate is rich in whey proteins, but also contains other components such as fat, lactose and glycomacroprotein (GMP), a casein-related non-globular protein. Typically, whey protein concentrate is produced by membrane filtration. On the other hand, whey protein isolate consists primarily of whey proteins with minimal amounts of fat and lactose. Whey protein isolate usually requires a more rigorous separation process such as a combination of microfiltration and ultra-filtration or ion exchange chromatography. It is generally understood that a whey protein isolate refers to a mixture in which at least 90 wt. % of the solids are whey proteins. A whey protein concentrate is understood as having a percentage of whey proteins between the initial amount in the by-product (about 12 wt. %) and a whey protein isolate. In particular, sweet whey, obtained as a by-product in the manufacturing of cheese, acid whey, obtained as a by-product in the manufacturing of acid casein, native whey, obtained by milk microfiltration or rennet whey, obtained as a by-product in the manufacturing of rennet casein, may be used as a source of whey proteins.

Furthermore, whey proteins may originate from all kinds of mammalian animal species, such as, for instance cows, sheep, goats, horses, buffalo's, and camels. Preferably, the whey protein is of bovine origin.

According to another embodiment, the proteinaceous matter according to the invention comprises at least about 45 wt. % of essential amino acids (EAA), preferably at least about 47 wt. %, and more preferably at least about 50 wt. % of EAA, based on total protein. Essential amino acids are amino acids selected from the group of isoleucine (Ile), leucine (Leu), lysine (Lys), methionine (Met), phenylalanine (Phe), threonine (Thr), tryptophan (Trp), and valine (Val). Since native whey protein and casein protein comprise (depending on the source) maximum about 45 and 41 weight % of EAA, respectively, it may be necessary to add EAA's to the nutritional composition, such as in the form of amino acids or peptides, to arrive at the preferred amount of at least 45 weight %.

Anabolic Amino Acids and Amino Acid Derivatives

The composition of the invention comprises leucine. Leucine is an anabolic amino acid, which is defined as an amino acid that promotes (hence, anabolic) muscle growth by increasing net protein synthesis. Preferably the composition for use comprises at least 10 wt. %, more preferably at least 12 wt. %, more preferably at least 14 wt. % leucine based on proteinaceous matter. Preferably the composition for use comprises at most 30 wt. %, more preferably at most 20 wt. % of leucine passed on proteinaceous matter. In case of a supplement it may be that the composition comprises at least 50 wt. %, more preferably at least 70 wt. %, even more preferably at least 90 wt. % and even more preferably at least 95 wt. % of leucine based on total protein. Preferably the supplement comprises at most 99 wt. %, more preferably 97 wt. % of leucine based on total protein.

Leucine is an essential amino acid, being part of a diverse number of proteins and, together with valine and isoleucine, belongs to the group of branched-chain amino acids. Leucine is known as a potent activator of muscle protein synthesis. Leucine may be used as a free amino acid, or in a bound form, such as a dipeptide, an oligopeptide, a polypeptide or a protein. Common protein sources of leucine are dairy proteins such as whey, casein, micellar casein, caseinate, and glycomacroprotein (GMP), and vegetable proteins such as wheat, rice, pea, lupine and soy proteins. It is hereby understood that bound leucine implies that the leucine is part of a larger molecule such as for instance a protein. Said sources of protein may provide intact proteins, hydrolysates or mixtures thereof, hereafter further called proteinaceous matter. Preferably the leucine is free L-leucine as this is very easy to digest. However, it is understood that protein sources comprising leucine will be broken-down to individual amine acids in the digestive tract.

In an embodiment, the total leucine—i.e. the sum of the free and bound leucine—is provided in a daily dosage of 5-25 g, preferably 10-20 g, more preferably 15-18 g. Whey typically comprises about 11 wt. % of leucine. It is considered that about 11 wt. % of total leucine based on the total amount of proteinaceous matter may be a minimum amount present in the nutritional composition. Preferably, said proteinaceous matter comprises at least about 12 wt. %, preferably at least about 12.5 wt. %, more preferably at least about 13 wt. % of total leucine based on total protein. Preferably said proteinaceous matter comprises at most 20 wt. %, more preferably at most 17 wt. %, more preferably at most 15 wt. % of total leucine based on total protein. In another embodiment the supplement composition comprises at least 50 wt. %, more preferably at least 60 wt. %, even more preferably at least 70 wt. % and even more preferably at least 80 wt. % of total leucine based on total protein. Preferably said supplement comprises at most 95 wt. %, more preferably at most 90 wt. % of leucine based on total protein.

Preferably the composition for use according to the invention comprises at least 5 wt. %, more preferably at least 7.5 wt. % and more preferably at least 10 wt. % of leucine based on the total composition, leucine being in free and/or bound form. Preferably the composition for use comprises less than 25 wt. %, preferably less than 20 wt. % and more preferably less than 15 wt. % of leucine based on the total composition, leucine being in free and/or bound form. In case of a supplement, the composition of the invention preferably comprises at least 25 wt. %, preferably at least 35 wt. %, more preferably at least 45 wt. % of leucine based on the total composition, leucine being in free and/or bound form.

Preferably at least 20 wt. %, preferably at least 25 wt. %, more preferably 30 wt., even more preferably at least 40 wt. %, even more preferably at least 50 wt. %, even more preferably at least 80 wt. %, more preferably at least 90 wt. %, and most preferably 100 wt. % (all) leucine or L-leucine is in the free form compared to the total amount of leucine.

In a preferred embodiment the composition for use of the invention comprises citrulline. Citrulline is an anabolic (α)-amino acid, which is defined as an amino acid that promotes (hence, anabolic) muscle growth by increasing net protein synthesis. A preferred amount of citrulline is 0.2-4 g per 100 g of the nutritional composition or 1-10 g per 100 g of the supplement. In one embodiment, citrulline is provided in a daily dosage of 0.5 to 10 g. Preferably, said proteinaceous matter comprises at least about 12 weight %, preferably at least about 12.5 weight %, more preferably at least about 13 weight % of citrulline based on total protein. Citrulline is an α-amino acid. Its name is derived from citrullus, the Latin word for watermelon, as it is naturally present in watermelons. Citrulline, in the form of citrulline malate, is sold as a performance-enhancing athletic dietary supplement which was suggested to promote aerobic energy production and to increase athletic performance and decreasing muscle soreness. In the human body, citrulline is produced from ornithine and carbamoyl phosphate in one of the central reactions in the urea cycle. It is also produced from arginine in the body as a by-product of the reaction catalyzed by NOS family. Citrulline is also capable of promoting muscle protein synthesis and has been described in human and animal studies. Citrulline is commercially available and can be obtained, e.g. from Ajinomoto, Kyowa, and Biocodex.

In a preferred embodiment, the composition for use of the invention comprises creatine. Creatine is an anabolic (α)-amino acid, which is defined as an amino acid that promotes (hence, anabolic) muscle growth by increasing net protein synthesis. A preferred amount of creatine is 0.2-4 g per 100 g of the nutritional composition or 1-10 g per 100 g of the supplement. In one embodiment, creatine is provided in a daily dosage of 0.5 to 20 g. Preferably, said proteinaceous matter comprises at least about 12 weight %, preferably at least about 12.5 weight %, more preferably at least about 13 weight % of creatine based on total protein. Creatine (N-(amino-imino-methyl)-N-methyl-glycine; methylglycocyamine) is a nitrogenous organic acid that is produced in vertebrates, in particular the human body from L-arginine, glycine, and L-methionine and helps to supply energy to muscles.

In one embodiment, any combination of leucine, citrulline, and creatine is provided in a daily dosage of 0.5 to 20 g, preferably 1 to 10 g. Any combination is a combination selected from the group of leucine and citrulline; leucine and creatine and leucine, citrulline and creatine.

Fibres

The composition for use according to the invention preferably further comprises one or more dietary fibres selected from the group of fructooligosaccharides (FOS), short chain fructooligosaccharides (scFOS), long chain fructooligosaccharides (lcFOS), and galactooligosaccharides (GOS).

The term dietary fibres, which is synonymous with "non-digestible oligosaccharides", as used in the present invention refers to carbohydrates which are not digested in the intestine by the action of acids or digestive enzymes present in the human upper digestive tract (small intestine and stomach) but which are preferably fermented by the human intestinal microbiota. For example, sucrose, lactose, maltose and maltodextrins are considered digestible. The term "oligosaccharide" as used in the present invention refers to carbohydrates with a degree of polymerization (DP) of 2 to 250, preferably a DP 2 to 100, more preferably 2 to 60, even more preferably 2 to 10. If the oligosaccharide with a DP of 2 to 100 is included in the present preparation, this includes compositions which contain oligosaccharides with a DP between 2 and 5, a DP between 50 and 70 and a DP of 7 to 60.

Preferably the non-digestible oligosaccharides are soluble. The term "soluble" as used herein, when having reference to an oligosaccharide, means that the oligosaccharide is soluble according to the method described by L. Prosky et al., J. Assoc. Off. Anal. Chem. 71, 1017-1023 (1988).

In a preferred embodiment the soluble indigestible fibers in the composition for use according to the present invention comprise fructooligosaccharides (FOS). The term "fructooligosaccharide" as used herein refers to a soluble indigestible fiber comprising a chain of at least 2 β-linked fructose units. A fructooligosaccharide can comprise a terminal glucose unit. In a preferred embodiment, the average degree of polymerisation of the fructooligosaccharides in the composition for use according to the present invention is in the range of 2 to 60, preferably the degree of polymerisation of the fructooligosaccharides is in the range from 2 to 60.

Preferably the soluble indigestible fibers in the composition for use according to the present invention is a combination of short chain fructooligosaccharides (scFOS) and long chain fructooligosaccharides (IcFOS). Preferably the ratio scFOS:IcFOS is in the range of 95/5 to 10/90, even more preferably in the range of 95/5 to 40/60. In the context of this invention, scFOS has an average DP between 2 and 6. In the context of this invention IcFOS means any fructooligosaccharide composition with an average DP larger or equal to 7. A suitable source of scFOS is RAFTILOSE® (Orafti). RARTILINE® HP (Orafti) is a particularly preferred source of IcFOS and has an average DP>20.

Preferably the non-digestible oligosaccharides comprise galacto-oligosaccharides (GOS). The galacto-oligosaccharides are preferably selected from the group consisting of beta-galacto-oligosaccharides. In a particularly preferred embodiment the present preparation comprises beta-galacto-oligosaccharides. Beta-galacto-oligosaccharides as used in the present invention refers to oligosaccharides composed of over 50%, preferably over 65% galactose units based on monomeric subunits, with a degree of polymerization (DP) of 2 to 20, in which at least 50%, more preferably at least 75%, even more preferably at least 90%, of the galactose units are linked together via a beta-glycosidic linkage, preferably a beta-1,4 glycosidic linkage. The average DP is preferably in the range of 3 to 6. A glucose unit may be present at the reducing end of the chain of galactose units. Beta-galacto-oligosaccharides are sometimes also referred to as transgalacto-oligosaccharides (TOS). A suitable source of beta-galacto-oligosaccharides is Vivinal®GOS (commercially available from Borculo Domo Ingredients, Zwolle, Netherlands). Other suitable sources are Oligomate (Yakult), Cupoligo, (Nissin) and Bi2muno (Classado).

In an embodiment of the present invention, the composition for use according to the invention comprises 0.5-6 g/100 kcal, more preferably 1-4 g/100 kcal of non-digestible carbohydrates.

Micronutrients

The nutritional composition for use according to the invention may optionally further comprise one or more micronutrients, defined as minerals, trace elements and vitamins, selected from the group of sodium, potassium, chloride, calcium, phosphorous, magnesium, carotenoids, vitamin A, vitamin E, vitamin K, vitamin B1, vitamin B2, vitamin B3, vitamin B5, vitamin B6, folic acid, vitamin B12, biotin, vitamin C, zinc, iron, copper, manganese, molybdenum, selenium, chromium, fluoride and iodide. Preferably, the micronutrients are selected from the group of carotenoids, vitamin A, vitamin B6, vitamin B12, vitamin C, vitamin E, folic acid, calcium, phosphorus, magnesium, zinc and selenium. Preferably, the nutritional composition according to the invention may further comprise carotenoids, vitamin B6, vitamin C, vitamin E, folic acid, vitamin B12, selenium and zinc.

The composition for use according to the invention preferably comprises 1-15, preferably 3-12, more preferably 5-10 μg of vitamin D per 100 mL of the composition. Vitamin D is well known in the art and is used to denote a group of fat-soluble secosteriods. Several forms of vitamin D exist, such as vitamin $D_1$ (ergocalciferol with lumisterol), vitamin $D_2$ (ergocalciferol), vitamin $D_3$ (cholecalciferol), vitamin Da (22-dihydroergocalciferol) and vitamin $D_5$ (sitocalciferol). Alternatively the composition for use according to the invention preferably comprises 2-20, preferably 5-15, more preferably 7-12 μg of vitamin D per 100 kcal. Preferably the vitamin D comprises at least 80 wt. %, more preferably at least 90 wt. %, and even more preferably at least 95 wt. % of vitamin $D_3$ (cholecalciferol) based on total weight of vitamin D.

The composition for use according to the invention preferably also comprises micronutrients such as carotenoids, vitamin A, vitamin B6, vitamin C, vitamin D3, vitamin E, folic acid, vitamin B12, selenium and/or zinc. Preferably, the nutritional composition for use according to the invention comprises per 100 kcal 10 to 500 mg of carotenoids, 8 to 750 μg of vitamin B6, 2.25 to 25 mg of vitamin C, 0.5 to 10 mg of vitamin E, 10 to 150 μg of folic acid, 0.07 to 5 μg of vitamin B12, 2.5 to 20 μg of selenium and 0.5 to 2.0 mg of zinc.

Medical Use

The nutritional composition according to the invention can advantageously be used for the prevention or treatment of a disease or condition involving muscle decline in a mammal, preferably a human of the age of 30 years of age or more, more preferably of the age of 50 years of age or more, most preferably in an elderly human. In this respect, it is submitted that in the context of this application, an elderly human is a person of the age of 50 years or more, in particular of the age of 55 or more, more in particular of the age of 60 or more, more in particular of the age of 65 or more. This definition takes into account the fact that the average age varies between different populations, on different continents, etc. Most developed world countries have accepted the chronological age of 65 years as a definition of 'elderly' or older person (associated with the age at which one may begin to receive pension benefits), but like many westernized concepts, this does not adapt well to e.g. the situation in Africa. At the moment, there is no United Nations (UN) standard numerical criterion, but the UN agreed cut-off is 60+ years to refer to the older population in Western world. The more traditional African definitions of an elder or 'elderly' person correlate with the chronological ages of 50 to 65 years, depending on the setting, the region and the country.

In a further preferred embodiment said human of the age of 30 years of age or more, more preferably of the age of 50 years of age or more, most preferably in an elderly human suffers from a disease or condition involving muscle decline such as sarcopenia, muscle degradation or any of the diseases or conditions further specified below.

Muscle decline comprises any disease or condition selected from the group of sarcopenia (loss of muscle mass related to aging, during or following body weight maintenance, during or following energy restriction, during or following bed rest, during or following physical trauma treatment (such as fractures) or during or following weightlessness), insufficient muscle protein synthesis, muscle degradation, impaired muscle recovery, muscle damage, muscle proteolysis, muscle atrophy, muscle dystrophy, muscle catabolism, muscle wasting, loss of muscle strength, loss of muscle function, loss of physical capacity, loss of physical performance, impaired mobility, frailty, disability, and risk of falling.

According to a further embodiment, the nutritional composition according to the invention or the supplement according to the invention can advantageously be used for the dietary management of a subject that is following a rehabilitation program and/or an exercise program.

According to a further embodiment, the nutritional composition according to the invention or the supplement according to the invention can advantageously be used for the dietary management of a subject that is suffering from overweight or obesity, said subject following a weight loss program, an energy restriction program, a rehabilitation program and/or an exercise program.

Muscle recovery refers to the structural or functional repair of the muscle tissue (cells, fibres, sarcomers). Muscle damage is the mechanical disruption of muscle fibre, its membrane or the surrounding connective tissue or tendons. Muscle degradation refers to the breakdown or loss of quality of muscle tissue. Muscle atrophy refers to the wasting or loss of muscle tissue resulting from disease or lack of use. Muscular dystrophy is characterized by progressive muscle weakness and loss of muscle tissue. Muscle wasting is the loss of muscle tissue resulting from disease or lack of use. Physical capacity is the ability to perform physical activity. Physical performance is the ability to perform a physical task (e.g. balance, gait speed, strength or endurance) at a desired level. Frailty is a condition referring to a collection of symptoms or markers primarily due to the aging-related loss and dysfunction of skeletal muscle, such as: reduced physical activity, muscle weakness, decreased performance, physical weakness, poor endurance, exhaustion, slow walking speed, low muscle strength. In elderly, frailty will increase the risk of adverse events such as death, disability, and institutionalization. Disability refers to the inability to perform a physical activity.

According to a further embodiment, the nutritional composition according to the invention or the supplement according to the invention can advantageously be used for the dietary management of sarcopenia, the age-related loss of muscle mass, strength and function.

According to a further embodiment, the nutritional composition according to the invention or the supplement according to the invention can advantageously be used for any one of the following in a mammal, alone or in combination:

support rebuilding muscle mass or muscle strength;

manage sarcopenia;

stimulate muscle protein synthesis, muscle strength, or muscle function;

support improved muscle protein synthesis, muscle strength, or muscle function;

improve or maintain mobility;

meet the needs of a sarcopenic mammal;

stimulate muscle protein synthesis;

increase muscle mass or muscle strength;

improve muscle strength or muscle function; and improve physical performance.

According to one embodiment, said mammal is a human of the age of 30 or more, more preferably of the age of 50 or more. More preferably, said mammal is an elderly human.

Dosage

The nutritional composition for use according to the invention is preferably administered as 1 to 2 servings daily, each serving comprising between 80 and 400 kcal, preferably 150-300 kcal. Preferably, the nutritional composition for use is administered as one serving daily. Using a nutritional composition in a liquid form, the serving may comprise 50 to 250 ml of nutritional composition for use according to the invention, most preferably 200 ml per serving. Using a nutritional composition in a solid form, such as a powder, the serving may comprise 20 to 100 g of nutritional composition according to the invention, most preferably 30 to 70 g per serving, most preferably about 40 g per serving.

The nutritional composition may be administered in a dosage regime, which may vary in time and according to the patient's needs. A typical regime comprises the administration of 1-3, preferably 2, servings daily during the treatment period, e.g. for about 3 months, optionally followed by the administration of one serving daily for prevention or as a maintenance dosage. The serving volume per administration is 75-150 ml, preferably 100-130 ml.

BRIEF DESCRIPTION OF THE FIGURES

FIG. 1 shows the results on puromycin incorporation of the in vitro study described in Example 1.

EXAMPLES

Example 1: In Vitro Experiment on Effects of EPA, MA and Leucine on Muscle Protein Synthesis An experimental in vitro study is performed to evaluate the synergistic or additional action of EPA, MA and leucine on intracellular pathways regulating protein synthesis in muscle cells.

C2C12 mouse myoblasts are obtained from the American Type Culture Source Collection (no. CRL-1772). Myoblasts are cultured at 37° C. in an atmosphere of 5% $CO_2$ in grown medium consisting of Dulbecco's modified Eagle's medium (DMEM) supplemented with 10% fetal calf serum and antibiotics. Myotube C2C12 differentiation is induced by withdrawing fetal calf serum from confluent cells and adding 10 µg/ml insulin, 5 µg/ml transferrin and 2% horse serum.

8-days-differentiated C2C12 myotubes are treated with medium containing EPA and/or MA for 16 hours. After a 4-hour starvation period, C2C12 myotubes were treated with insulin (100 nM)+Leucine (5 mM) for in total 60 min. A limitation of growing myotubes in vitro is that the cells are not able to produce insulin when administered leucine whereas in vivo the pancreas starts producing insulin when leucine is administered to a subject. Common to this model, to compensate for this limitation, the in vitro experiment requires the separate administration of insulin. Subsequently, a protein synthesis label (puromycin) was added to the medium and the tubes were homogenized in lysis buffer. By western-Blot analyses the level of protein synthesis was analyzed. This gives quantitative information on the incorporation of puromycin which is a measure for intracellular pathways regulating protein synthesis (Akt, mTOR) and/or a direct measure of protein synthesis. Hence the results are indicative for the prevention and/or treatment of a disease or condition involving muscle decline or for improving muscle function.

The model is widely applied in the art, to the same end i.e. drawing conclusions on muscle protein synthesis, muscle mass and muscle function. Reference is made to Brooks Mobley et al. "whey protein-derived exosomes increase protein synthesis and hypertrophy in C2C12 myotubes" J. Dairy Sci. 100:48-64 (2006); Jing et al. "alpha-lipoic acids promote the protein synthesis of C2C12 myotubes by the TLR2/PI13K signalling pathway" J. Agric. Food Chem. 2016, 64, 1720-1729; and Salles et al. "1,25(OH)2-vitamin D3 enhances the stimulating effect of leucine and insulin on protein synthesis rate through Akt/PKB and mTOR mediated pathways in murine C2C12 skeletal myotubes" Mol. Nutr. Food Res. 2013, 00, 1-10.

The above-described myoblasts were supplemented with various amounts of EPA and MA to assess their synergistic or additional action. The experimental legs all have muscle stimulation in the form of insulin and leucine. There is a control without stimulation and without fatty acids and there is a control with stimulation and without fatty acids. The experimental legs have:

25 µM of EPA without MA,

25 µM of MA without EPA,

50 µM of MA without EPA,

25 µM of EPA and 25 µM of MA (molar ratio 1:1 which is equivalent to a weight ratio of 1.3:1), 25 µM of EPA and 50 µM of MA (molar ratio of 1:2 which is equivalent to a weight ratio of 0.66:1).

The results are presented in the FIG. 1. All results are relative to the control without any stimulation and without fatty acids (the control is indexed at 100). As can be seen from the graph, both EPA and MA individually have an effect on puromycin incorporation. However the effect of puromycin incorporation of EPA and MA is much larger when added simultaneously compared to the effects of the individual fatty acids. This effect even surpasses the sum of the individual effects relative to the control. Hence EPA and MA act in a synergistic manner when added simultaneously.

Furthermore, it is shown that the ratio of EPA to MA is more important than the total level of fatty acids, as raising the level of from 25 µM MA to 50 µM MA had a much smaller effect than adding 25 µM of EPA to 25 µM of MA.

In addition, the bar showing the incorporation of puromycin incorporation for 25 µM EPA and 50 µM MA (i.e. molar ratio of 1:2 which corresponds to a weight ratio of 0.66:1) is significantly lower than the bar for 25 µM of each (which corresponds to a weight ratio of 1.3:1).

The invention claimed is:

1. A method for improving muscle function in a subject, by administering to the subject a composition comprising eicosapentaenoic acid (20:5(n-3); EPA), myristic acid (C14: 0; MA) and leucine, wherein the composition comprises EPA and MA in a weight ratio in the range of 1.0:1-1.6:1.

2. The method according to claim 1, wherein improving muscle function involves gaining muscle mass and/or maintaining muscle mass.

3. The method according to claim 1, wherein improving muscle function involves improving muscle protein synthesis.

4. The method according to claim 1, wherein the composition comprises less than 5 wt. % DHA based on total fatty acids.

5. The method according to claim 1, wherein the composition comprises 0.1-1 g EPA per 100 ml of the composition.

6. The method according to claim 1, wherein at least 50 wt. % of the EPA and/or the MA is provided as free fatty acid.

7. The method according to claim 6, wherein all of the EPA and MA is provided as free fatty acid.

8. The method according to claim 1, wherein the composition comprises whey protein.

9. The method according to claim 1, wherein the composition comprises at least 11 wt. % leucine based on total proteinaceous matter in the composition.

10. The method according to claim 1, wherein the composition comprises at least 20 wt. % of leucine in a free form, relative to the total amount of leucine.

11. The method according to claim 1, wherein the composition further comprises one or more dietary fibres.

12. The method according to claim 1, wherein the composition further comprises carotenoids, vitamin A, vitamin B6, vitamin C, vitamin D3, vitamin E, folic acid, vitamin B12, selenium and/or zinc.

13. The method according to claim 1, wherein the composition is a supplement.

14. The method according to claim 1, wherein the subject is suffering from overweight or obesity, said subject following a weight loss program, an energy restriction program, a rehabilitation program and/or an exercise program.

15. The method according to claim 1, wherein improving muscle function involves rebuilding muscle mass or muscle strength, manage sarcopenia, stimulate muscle protein synthesis, improve and/or maintain mobility, and/or improve physical performance.

* * * * *